United States Patent
Emburgh et al.

(10) Patent No.: US 9,844,782 B2
(45) Date of Patent: Dec. 19, 2017

(54) SYSTEMS AND METHODS FOR PREPARING SAMPLES FOR CHEMICAL ANALYSIS USING A COOLED DIGESTION ZONE

(71) Applicant: 7685297 Canada Inc., London (CA)

(72) Inventors: Ron J. Emburgh, Mississauga (CA); Ravi K. Kanipayor, London (CA)

(73) Assignee: ColdBlock Technologies Inc., St. Catherines, Ontario (CA)

( * ) Notice: Subject to any disclaimer, the term of this patent is extended or adjusted under 35 U.S.C. 154(b) by 468 days.

(21) Appl. No.: 14/307,642

(22) Filed: Jun. 18, 2014

(65) Prior Publication Data
US 2014/0377880 A1 Dec. 25, 2014

Related U.S. Application Data

(60) Provisional application No. 61/837,836, filed on Jun. 21, 2013.

(51) Int. Cl.
*B01L 7/00* (2006.01)
*G01N 1/34* (2006.01)
(Continued)

(52) U.S. Cl.
CPC ........ *B01L 7/00* (2013.01); *B01L 3/04* (2013.01); *G01N 1/34* (2013.01); *G01N 1/44* (2013.01);
(Continued)

(58) Field of Classification Search
CPC .......................................................... B01L 7/00
(Continued)

(56) References Cited

U.S. PATENT DOCUMENTS

| | | | |
|---|---|---|---|
| 3,715,189 A | | 2/1973 | Nighohossian et al. |
| 4,835,354 A | * | 5/1989 | Collins ............... B01L 7/00 |
| | | | 219/746 |

(Continued)

FOREIGN PATENT DOCUMENTS

| | | | | |
|---|---|---|---|---|
| CA | WO 2011054086 A1 | * | 5/2011 | ........ B01L 3/04 |
| CN | 2527998 Y | | 12/2002 | |

(Continued)

OTHER PUBLICATIONS

European Patent Office, Extended European Search Report dated Feb. 22, 2016, issued on corresponding European application No. 10827750.0.

(Continued)

*Primary Examiner* — Christopher A Hixson
*Assistant Examiner* — Emily Berkeley
(74) *Attorney, Agent, or Firm* — Bereskin & Parr LLP

(57) ABSTRACT

An apparatus for preparing samples for chemical analysis includes a container receptacle for receiving a sample container having a crucible portion and an expansion portion. The container receptacle includes a heating compartment and a cooling compartment spaced apart from the heating compartment. The heating compartment is shaped to receive the crucible portion of the sample container, and the cooling compartment is shaped to receive the expansion portion of the sample container. The apparatus also includes a heating mechanism for heating the sample within the crucible portion of the sample container, a first cooling mechanism for cooling the expansion portion of the sample container, and a second cooling mechanism for cooling the crucible portion of the sample container.

28 Claims, 6 Drawing Sheets

(51) Int. Cl.
*B01L 3/04* (2006.01)
*G01N 1/44* (2006.01)
*G01N 21/03* (2006.01)
*G01N 1/40* (2006.01)

(52) U.S. Cl.
CPC ... *B01L 2300/18* (2013.01); *B01L 2300/1822* (2013.01); *B01L 2300/1844* (2013.01); *B01L 2300/1872* (2013.01); *B01L 2300/1894* (2013.01); *G01N 1/4044* (2013.01); *G01N 21/0332* (2013.01); *Y10T 436/25* (2015.01); *Y10T 436/25125* (2015.01)

(58) Field of Classification Search
USPC .......................................................... 436/175
See application file for complete search history.

(56) References Cited

U.S. PATENT DOCUMENTS

| | | | |
|---|---|---|---|
| 5,085,759 | A | 2/1992 | Harker |
| 5,114,858 | A | 5/1992 | Williams et al. |
| 5,215,715 | A | 6/1993 | Haswell et al. |
| 5,281,516 | A | 1/1994 | Stapleton et al. |
| 5,298,276 | A * | 3/1994 | Jayaraman ............... A61F 2/06 427/2.25 |
| 5,306,896 | A | 4/1994 | Glater et al. |
| 6,440,746 | B1 * | 8/2002 | Troxler ................... G01N 5/04 110/236 |
| 2001/0017060 | A1 | 8/2001 | Offen et al. |
| 2002/0198230 | A1 | 12/2002 | Kingston |
| 2004/0159167 | A1 | 8/2004 | Bremer et al. |
| 2007/0014690 | A1 | 1/2007 | Lawrence et al. |
| 2007/0210090 | A1 | 9/2007 | Sixt et al. |
| 2007/0275478 | A1 | 11/2007 | Taranenko et al. |
| 2008/0046044 | A1 | 2/2008 | Jahnigen et al. |
| 2008/0072689 | A1 | 3/2008 | Muraishi et al. |
| 2008/0168847 | A1 | 7/2008 | Poo et al. |
| 2008/0229849 | A1 | 9/2008 | Doebler et al. |
| 2011/0239792 | A1 | 10/2011 | Sato et al. |
| 2013/0125673 | A1 | 5/2013 | Kanipayor et al. |

FOREIGN PATENT DOCUMENTS

| | | |
|---|---|---|
| CN | 201335809 Y | 10/2009 |
| DE | 10150475 | 4/2003 |
| DE | 10150475 A1 | 4/2003 |
| EP | 2295961 | 3/2011 |
| WO | WO9820341 | 5/1998 |
| WO | WO03036263 | 5/2003 |
| WO | 2009/136694 A2 | 11/2009 |
| WO | WO2011054086 | 5/2011 |

OTHER PUBLICATIONS

Google Patents, English translation of DE10150475
Google Patents, English translation of Abstract of WO2009/1366694.
Infra-red Heating as an Alternative Technique for Fast Sample Preparation, Gouveia et al., Journal of the Brazilian Chemical Society, vol. 11, No. 3, pp. 261-265, (2000).
Nanoparticles produced by laser ablation of solids in liquid environment, Simakin et al., Applied Physics A—Materials Science & Processing, vol. 79, pp. 1127-1132, (2004).
International Searching Authority, Written Opinion and International Search Report for PCT/CA2010/001734, dated Mar. 7, 2011.
Chinese Patent Office, Office Action, for Chinese Patent Application Serial No. 201080060258.0 dated Mar. 14, 2014.
English Translation of Abstract only, Chinese Patent Application Serial No. CN201335809Y.
English Translation of Abstract Only, Chinese Patent Application Serial No. CN2527998Y.
International Searching Authority, Written Opinion and International Search Report for PCT/CA2014/000511, dated Sep. 22, 2014.
European Patent Office, Extended European Search Report for European Patent Application No. 14813225.1, dated Jan. 5, 2017.

* cited by examiner

SYSTEMS AND METHODS FOR PREPARING SAMPLES FOR CHEMICAL ANALYSIS USING A COOLED DIGESTION ZONE

RELATED APPLICATIONS

This application claims priority to U.S. Provisional Patent Application No. 61/837,836, filed on 21 Jun. 2013, and entitled "SYSTEMS AND METHODS FOR PREPARING SAMPLES FOR CHEMICAL ANALYSIS USING A COOLED DIGESTION ZONE".

TECHNICAL FIELD

The embodiments herein relate to preparing samples for chemical analysis, and in particular to apparatus, systems and methods for dissolving samples into a liquid prior to undergoing chemical analysis.

BACKGROUND

Chemical analysis of samples often begins with a sample preparation process to bring an analytical component of interest (the "analyte") from a solid/semi-solid matrix into aqueous medium or another liquid form. This is because many laboratory instruments used for chemical analysis rely upon analyzing the sample in liquid form. Such laboratory instruments include Inductively Coupled Plasma (ICP), Inductively Couple Plasma Mass Spectrometers (ICPMS), and Atomic Absorption Spectrometers.

The types of samples undergoing sample preparation prior to analysis are diverse and include wastewater, sludge, sediments, soils, rocks, foods, powder, industrial and manufactured products, animal and plant tissue, plastics, oils, steel, greases, coal, cements, and paint chips. The areas of analytical applications are also diverse and include environmental, geological, food, agriculture, forestry, pharmaceutical, and industrial quality control. One common trait among these applications is that, in most cases, the sample undergoes sample preparation before analyzing the sample. There are different types of sample preparation procedures for dissolving the analyte into liquid form such as digestion or another type of dissolution. The following are a few examples of these sample preparation procedures.

Acid digestion is a procedure in which a sample reacts with an acid to dissolve the sample partially or completely into liquid form. Generally, acid digestion is carried out in a beaker placed on a hot plate. This procedure uses large volumes of volatile acids, which can evaporate and escape into the environment, and thus represents an environmental concern. Accordingly, acid vapors are often vented into large expensive fume hoods with exhaust scrubbers. Unfortunately, the scrubbers produce large volumes of acidified wastewater, which still represents an environmental disposal issue. Acid digestion also has a number of other problems. In particular, acid digestion can take many hours, involves continuous monitoring, and tends to be manual and labor intensive. Acid digestion is also prone to loss of the analyte through vaporization, contamination problems, and generally has poor precision. It is also difficult to automate and computerize the acid digestion process. The handling of hot acid also represents a safety concern.

In some laboratories, acid digestions are performed using "hot block" digestion vessels, which are large heated blocks having a number of openings for receiving test tubes containing samples and acid. While this allows some degree of automation and control, acid digestion in a hot block is still prone to the other disadvantages noted above.

Microwave acid digestion is another sample preparation process whereby a sample and acid are placed into a closed vessel and heated by microwave radiation. Volatile elements are contained within the closed vessel, which can offer better control of exhaust fumes and can reduce environmental impact. Microwave acid digestion also tends to use less acid compared to hot block digestion because the acid is contained within the closed vessel. However, microwave acid digestion still suffers from a number of problems. For example, some samples can take longer to digest in comparison to acid digestion in a beaker or hot block. Furthermore, the pressurized closed vessels can be expensive to make, hard to clean, and difficult to work with. Sample sizes are often limited to 0.2-1.0 grams. Another drawback is that the digestion vessel is often made from TEFLON™, which limits the maximum digestion temperature to about 245° C., otherwise the TEFLON™ lining might distort or deteriorate and can contaminate the sample. With these limitations, microwave digestion can be hard to automate, expensive, and typically results in low production rates with limited batch capacity. Accordingly, while microwave acid digestion might be appropriate for low volume laboratories that focus on digesting certain difficult samples, the process is less attractive to high volume laboratories, which tend to focus on productivity and costs while analyzing a diverse range of samples.

Apparatus, systems and methods for preparing samples for chemical analysis are described in PCT Patent Application No. WO2011/054086, which was filed in the name of the present inventors. The system comprises at least one sample container, and a container receptacle apparatus for receiving the sample container. The sample container comprises an elongate tubular body having a crucible portion proximal to a closed end for receiving a sample therein, and an expansion portion proximal to an open end. The container receptacle apparatus comprises a housing having a heating compartment, a cooling compartment spaced apart from the heating compartment, and an insulating region located between the heating compartment and the cooling compartment. The heating compartment is shaped to receive the crucible portion of the sample container, and the cooling compartment is shaped to receive the expansion portion of the sample container. The apparatus also includes a heating mechanism for heating the sample within the crucible portion of the sample container, and a cooling mechanism for cooling the expansion portion of the sample container.

While the apparatus, systems and methods described in WO2011/054086 were capable of overcoming one or more of the problems identified above in respect of conventional sample preparation procedures, the inventors have made further refinements and improvements as now described herein.

SUMMARY

According to some embodiments, there is an apparatus for preparing samples for chemical analysis. The apparatus includes a container receptacle for receiving at least one sample container having a crucible portion and an expansion portion. The container receptacle includes a heating compartment and a cooling compartment spaced apart from the heating compartment. The heating compartment is shaped to receive the crucible portion of the sample container, and the cooling compartment is shaped to receive the expansion portion of the sample container. The apparatus also includes a heating mechanism for heating the sample within the crucible portion of the sample container while the sample container is received within the container receptacle, a first cooling mechanism for cooling the expansion portion of the sample container while the sample container is received within the container receptacle, and a second cooling mechanism for cooling the crucible portion of the sample container while the sample container is received within the container receptacle.

The second cooling mechanism may include a fan located within the heating compartment. The fan may have a variable speed. The apparatus may also include a controller for controlling speed of the fan.

The first cooling mechanism may include a thermoelectric cooler within the cooling compartment. The first cooling mechanism may include a refrigeration unit within the cooling compartment.

The second cooling mechanism may include a refrigeration unit within the heating compartment.

The first cooling mechanism may be configured to cool both the expansion portion and the crucible portion of the sample container.

The heating mechanism may include an infrared heater disposed within the heating compartment for emitting infrared radiation.

According to some embodiments, there is a system for preparing samples for chemical analysis. The system includes a sample container including an elongate tubular body extending from an open end to a closed end, a crucible portion proximal to the closed end for holding a sample to be analyzed, and an expansion portion proximal to the open end. The system also includes a container receptacle for receiving the sample container. The container receptacle includes a heating compartment, and a cooling compartment spaced apart from the heating compartment. The heating compartment is shaped to receive the crucible portion of the sample container, and the cooling compartment is shaped to receive the expansion portion of the sample container. The system also includes at least one heating mechanism for heating the sample within the crucible portion of the sample container while the sample container is received within the container receptacle, a first cooling mechanism for cooling the expansion portion of the sample container, and a second cooling mechanism for cooling the crucible portion of the sample container.

The heating mechanism may be configured to emit infrared radiation that is selected to be absorbed by the sample in the crucible portion of the sample container. Furthermore, the crucible portion may be substantially transparent to the infrared radiation. For example, the sample container may be made of quartz.

The heating mechanism may include an infrared heater disposed within the heating compartment for emitting the infrared radiation. The infrared heater may include at least two infrared heater rings that are sized and shaped to receive and encircle the crucible portion of the sample container. One or more of the infrared heater rings may be moveable lengthwise along the crucible portion of the sample container.

According to some embodiments, there is a sample container for preparing samples for chemical analysis. The sample container includes an elongate tubular body extending from an open end to a closed end. The tubular body has a crucible portion proximal to the closed end for receiving a sample therein, and an expansion portion proximal to the open end. The crucible portion has a smaller diameter than the expansion portion. The tubular body is sized and shaped to be received within a container receptacle having a cooling compartment and heating compartment such that the expansion portion is shaped to be received within the cooling compartment and the crucible portion is shaped to be received within the heating compartment. The crucible portion includes an inner crucible wall and an outer crucible wall spaced apart from the inner crucible wall.

The crucible portion may be made of quartz.

The outer crucible wall may have an inlet and an outlet for supplying a coolant between the inner crucible wall and the outer crucible wall.

According to some embodiments, there is a method for preparing samples for chemical analysis. The method includes: placing a sample within a sample container containing an acid, the sample container having a crucible portion for receiving the sample and an expansion portion; heating the sample within the crucible portion of the sample container; cooling the expansion portion of the sample container contemporaneously with the heating of the sample; and cooling the crucible portion of the sample container contemporaneously with the heating of the sample.

The crucible portion may be cooled using at least one fan. For example, the at least one fan may supply cooler air to the crucible portion, or may remove hot air from the crucible portion, or a combination there of.

The expansion portion may be cooled using a thermoelectric cooler.

The expansion portion and the crucible portion may be cooled using at least one refrigeration unit.

The sample may be heated using infrared radiation that is selected to be absorbed by the sample in the crucible portion of the sample container. Furthermore, the crucible portion may be substantially transparent to the infrared radiation. For example, the sample container may be made of quartz.

The method may also include placing the acid within the crucible portion of the sample container. The acid may include hydrofluoric acid.

The sample may be heated using at least one infrared heater ring that is sized and shaped to receive and encircle the crucible portion of the sample container, and the method may include moving the infrared heater ring lengthwise along the crucible portion of the sample container. Furthermore, the sample may be heated using at least two infrared heater rings.

The method may also include placing the sample container into a container receptacle prior to heating the sample.

According to some embodiments, there is an apparatus for preparing samples for chemical analysis. The apparatus includes a container receptacle for receiving at least one sample container having a crucible portion and an expansion portion. The container receptacle includes a heating compartment and a cooling compartment spaced apart from the heating compartment. The heating compartment is shaped to receive the crucible portion of the sample container, and the cooling compartment is shaped to receive the expansion portion of the sample container. The apparatus also includes a heating mechanism for heating the sample within the crucible portion of the sample container while the sample container is received within the container receptacle, and at least one cooling mechanism for cooling the expansion portion and the crucible portion of the sample container while the sample container is received within the container receptacle.

The at least one cooling mechanism may include a first cooling mechanism for cooling the expansion portion of the sample container, and a second cooling mechanism for cooling the crucible portion of the sample container.

Other aspects and features of the specification will become apparent, to those ordinarily skilled in the art, upon review of the following description of some exemplary embodiments.

BRIEF DESCRIPTION OF THE DRAWINGS

Some embodiments of the present specification will now be described, by way of example only, with reference to the following drawings, in which.

DETAILED DESCRIPTION

During sample digestion, chemical reaction dynamics are generally defined by the amount of energy available for the reactions. Thus, in theory, increasing the energy input usually increases the energy available for sample digestion, which can reduce digestion time. However, a limiting factor for energy input to chemical reactions in a sample digestion is the vaporization of liquid reactants such as the acid used for the digestion. As the acid vaporizes beyond its boiling point, the reactants are no longer in contact with the solid sample being digested, which slows digestion. Accordingly, in a conventional digestion process, increasing input energy does not necessarily speed up digestion, and on the contrary, may cause longer digestion time due to acid vaporization.

Previous "hot block" digestion systems tend to address acid vaporization by limiting the amount of input energy as a balance to minimize loss of acids and volatile components. However, the decreased input energy can make it harder to digest samples and can increase digestion time.

In contrast to "hot block" digestion systems, microwave digestion systems address acid vaporization by using a closed system. The closed system tends to prevent vaporized reactants from escaping the sample container while also increasing pressure to elevate the boiling point of the liquid reactants. However, microwave radiation can still have significant vaporization. One reason for this is that microwave radiation is usually absorbed by the liquid reactant (e.g. water molecules of the acid). Thus, the liquid reactants are heated first, which then heats the sample in order to initiate digestion. Heating the liquid reactants first can be inefficient because some of the acid may vaporizes, which can reduce digestion performance.

The system described in PCT Patent Application No. WO2011/054086 is capable of condensing vaporized acid and refluxing them back to a digestion zone within the sample container. For example, as acid boils and vaporizes within the crucible portion of the sample container, the expansion portion of the sample container is cooled to condense the acid vapors and volatile analytes, and reflux them back to the crucible portion. While this can reduce the loss of acid and analytes under certain conditions, there may still be boiling within the crucible portion, which can decrease digestion performance and can limit the amount of effective input energy.

In view of the above, it has been recognized that it can be desirable to reduce boiling of the acid and other liquid reactants in the hot digestion zone. This can help increase sample dissolution performance, for example, by allowing increased input energy as will be described later below.

Figure 1:
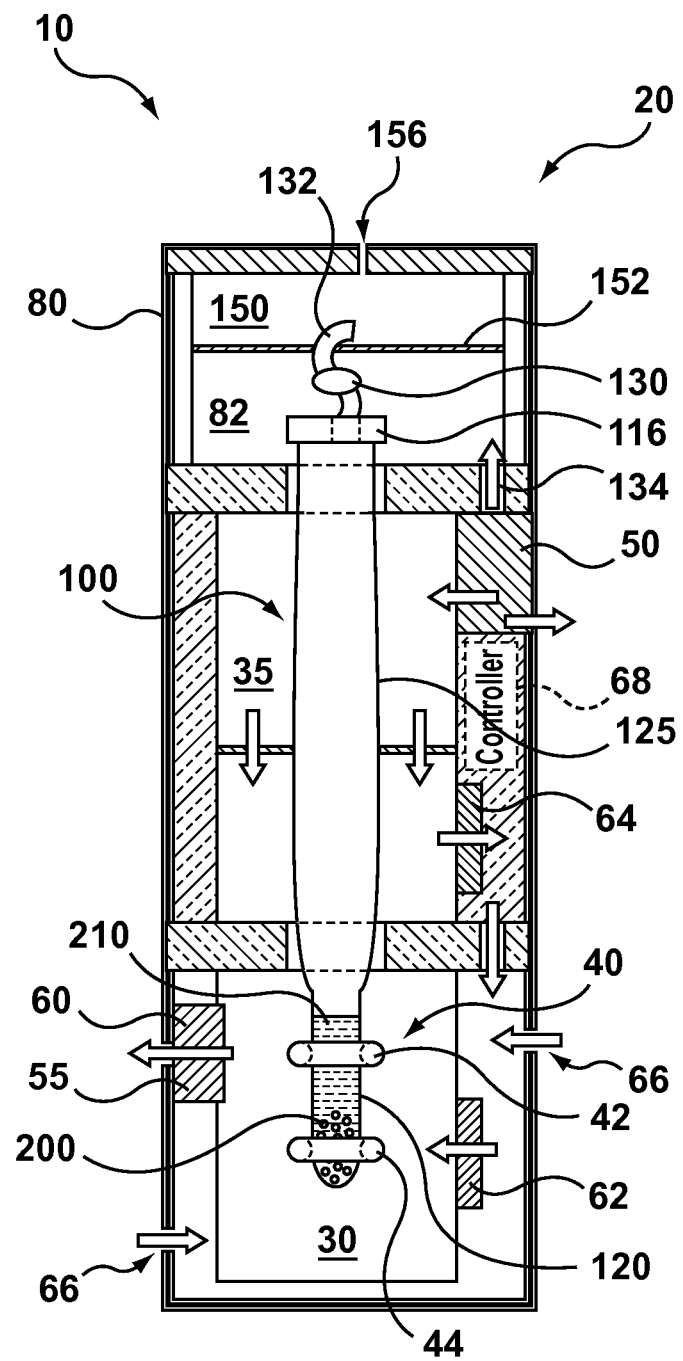
FIG. 1 is a schematic cross-sectional view of an apparatus for preparing samples for chemical analysis according to one embodiment.

Referring now to FIG. 1, illustrated therein is a sample preparation apparatus 10 made in accordance with an embodiment of the present invention. The apparatus 10 includes a container receptacle 20 for receiving a sample container 100. The sample container 100 holds a sample 200 to be digested, and a liquid reactant such as an acid 210. The sample 200 may be a solid such as sediment, soil, rock, food, plants, powder, organic tissue, plastic, metal, coal, cement, paint chip, combinations thereof, and the like. The acid 210 may be nitric acid, hydrochloric acid, hydrofluoric acid, perchloric acid, sulphuric acid, phosphoric acid, an acid mixture such as aqua regia, or another type of acid or acid mixture.

Figure 2:
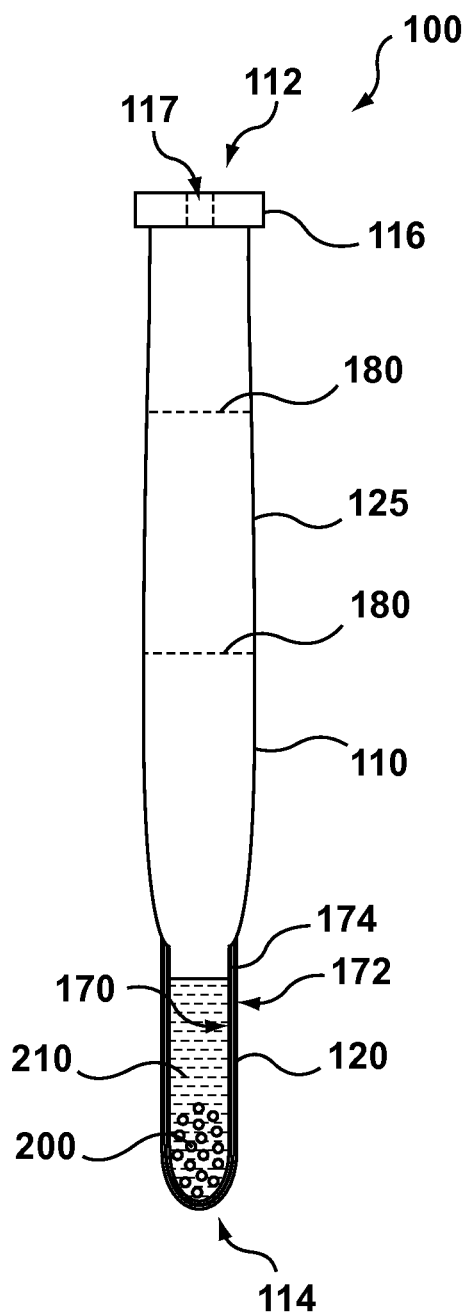
FIG. 2 is a schematic cross-sectional view of a sample container of the apparatus of FIG. 1.

With reference to FIG. 2, the sample container 100 includes an elongate tubular body 110 extending from an open end 112 to a closed end 114. The sample container 100 also includes a crucible portion 120 proximal to the closed end 114, and an expansion portion 125 proximal to the open end 112. The crucible portion 120 generally holds the sample 200 during sample preparation, which may include drying, ashing, digestion, and/or dissolution. The open end 112 allows insertion of the sample 200 and the acid 210 into the crucible portion 120. A lid 116 may cover or seal the open end 112 to enclose the sample container 100. Other features of the sample container 100 will be described later below.

Figure 3:
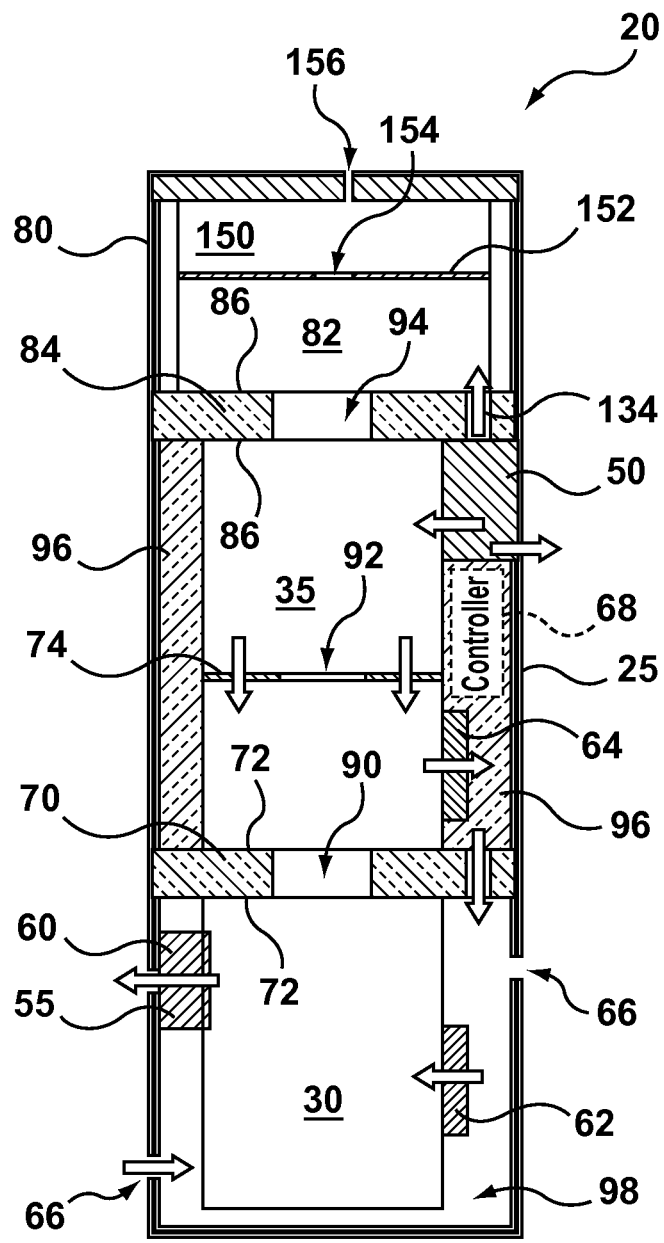
FIG. 3 is a schematic cross-sectional view of a container receptacle of the apparatus of FIG. 1.

Referring now to FIG. 3, the container receptacle 20 includes a housing 25 having a heating compartment 30, and a cooling compartment 35 spaced apart from the heating compartment 30. As shown, the cooling compartment 35 is located above the heating compartment 30. The heating compartment 30 is generally shaped to receive the crucible portion 120 of the sample container 100, and the cooling compartment 35 is generally shaped to receive the expansion portion 125 of the sample container 100. For example, the housing 25 may have a generally cylindrical or tubular cavity for receiving the crucible portion 120 within the heating compartment 30, and for receiving the expansion portion 125 within the cooling compartment 35.

Referring again to FIG. 1, the apparatus 10 also includes one or more heating mechanisms 40 for heating the sample 200 within the crucible portion 120 of the sample container 100. In the illustrated embodiment, the heating mechanism 40 is configured to emit infrared radiation towards the sample 200 within the crucible portion 120. The wavelength of the infrared radiation is generally selected to be absorbed by the sample 200 so as to heat the sample 200. For example, the infrared radiation may have a wavelength of between about 700-nm and about 1-mm. More particularly, the infrared radiation may have a wavelength of less than about 3-μm, or more particularly still, less than about 1.4-μm. In some cases, the infrared radiation may have a peak energy at about 1-μm.

In the illustrated embodiment, the heating mechanism 40 includes two infrared heater rings 42, 44 located within the heating compartment 30. The infrared heater rings 42, 44 are sized and shaped to receive and encircle the crucible portion 120. As an example, the infrared heater rings 42, 44 may be omega-style infrared rings having a quartz tube, ceramic or gold reflectors, halogen or tungsten filaments, and a max power of 250 W. Such infrared rings are sold by Anderson Thermal Devices Inc., for example, under product number OMG02511549C45. These infrared rings are capable of emitting short infrared wavelengths of about 1.15-μm at peak energy with filament temperatures of up to about 2400° C.

In other embodiments, there may be a different number of infrared heater rings, such as one or more infrared heater rings. Furthermore, the heating mechanism 40 may include other types of infrared heaters or other sources of infrared radiation.

The apparatus 10 also includes a first cooling mechanism 50 for cooling the expansion portion 125 of the sample container 100, and a second cooling mechanism 55 for cooling the crucible portion 120 of the sample container 100. In the illustrated embodiment, the first cooling mechanism 50 includes a thermoelectric cooler such as a Peltier cooler, and the second cooling mechanism 55 includes a fan such as a variable speed exhaust fan. In other embodiments, the cooling mechanisms could include other types of thermoelectric coolers, fans, refrigeration units, heat pumps, and the like, or combinations thereof. Furthermore, a single cooling mechanism could be used to cool both the crucible portion 120 and the expansion portion 125.

The first cooling mechanism 50 cools the expansion portion 125 of the sample container 100. Cooling the expansion portion 125 of the sample container 100 can help counteract vaporization by reflux condensation of the acid 210 when heating the sample 200. For example, when the sample 200 is heated during digestion, some of the acid 210 may evaporate and rise to the expansion portion 125. The first cooling mechanism 50 may help condense and reflux the acid vapors back to the crucible portion 120.

In the illustrated embodiment, the first cooling mechanism 50 circulates cool or cold air within the cooling compartment 35 (e.g. using one or more fans within the cooling compartment). For example, the first cooling mechanism 50 may be configured to maintain the cooling compartment 35 at a desired cooling temperature of, for example, less than about 10° C., or more particularly, less than about 5° C. Circulating air within the cooling compartment 35 can indirectly cool the expansion portion 125 of the sample container 100.

In other embodiments, the first cooling mechanism 50 may cool the expansion portion 125 in other ways, which may include direct or indirect cooling. For example, another type of coolant or cooling medium may indirectly cool the expansion portion 125 (e.g. using a refrigeration unit). Alternatively, the expansion portion 125 may be cooled through conductive heat transfer, for example, using a cooling block, in which the first cooling mechanism 50 cools the block, which then cools the expansion portion 125. The second cooling mechanism 55 could also use these and other cooling techniques.

The second cooling mechanism 55 cools the crucible portion 120 of the sample container 100. For example, the second cooling mechanism 55 may circulate cool or cold air within the heating compartment 30 to maintain the heating compartment 30 at a desired cooling temperature. This can indirectly cool the crucible portion 120 of the sample container 100, which in turn, can remove heat from the acid 210 in the crucible portion 120.

Removing heat from the acid 210 can be desirable in order to help maintain the temperature of the acid 210 below its boiling point or reduce boiling of the acid. This can help reduce vaporization as described above. Moreover, less vaporization can also reduce the amount of cooling for maintaining the expansion portion 125 of the sample container 100 at a desired temperature.

The second cooling mechanism 55 is generally configured to maintain the heating compartment 30 at a temperature below the boiling point of the acid 210 or other liquid reactants. In some embodiments the second cooling mechanism 55 may be configured to maintain the heating compartment 30 at a temperature of below 100° C., or more particularly, near room temperature (e.g. about 20-22° C.). This may be useful when using the acid 210 or other liquid reactants have a boiling point near 100° C. (which is common with aqueous solutions and some acids such as hydrochloric acid, nitric acid, and hydrofluoric acid). In other examples, the temperature may be higher or lower. For example, sulphuric acid and phosphoric acid have higher boiling points near 300° C., and in such cases, the second cooling mechanism 55 may be configured to maintain the heating compartment 30 at a temperature below 300° C.

The removal of heat from the acid 210 through the crucible portion 120 can also allow an increase of input energy to the sample 200. While this may seem counterintuitive, this is believed to enhance sample digestion based upon the following theory described below.

As described previously, the heating mechanism 40 may be selected to emit infrared radiation that is absorbed by the sample 200. The infrared radiation may also be selected to be partially or completely transmitted through the sample container 100 and the acid 210. Thus, the infrared radiation may be selected to directly heat the sample 200 without appreciably heating the sample container 100 or the acid 210.

For example, liquid reactants such as acids and other aqueous solutions tend to be more transparent to infrared radiation as compared to microwave radiation, particularly for near-infrared and short infrared wavelengths. Accordingly, infrared radiation can offer a greater amount of input radiation energy to energize the sample 200 directly, and thereby initiate chemical transformation of the sample in the presence of the liquid reactant (e.g. the acid 210). Furthermore, excess thermal energy released from transformation of the sample 200 to the acid 210 can be removed by the second cooling mechanism 55, which can help maintain the temperature of the acid 210 below its boiling point.

Thus, removal of thermal energy from the acid 210, though against conventional theories, can enhance sample digestion and can allow more input energy to further enhance or speed up the digestion process. In some examples, the increased input energy may be equivalent to 800° to 900° C. at the surface of the sample 200, which can provide faster sample decomposition or allow more complete digestion of difficult samples. Moreover, in some examples, the infrared heater rings 42, 44 may be capable of producing temperatures of up to 2000° C. at the surface of the sample 200, which can further enhance sample decomposition.

In some embodiments, it may be desirable to pressurize the sample container 100 during digestion. For example, increased pressure in the crucible portion 120 can increase the boiling points of the acid or other liquids. This can help reduce vaporization of both the acid and analytes while also allowing even more input energy to the sample 200. Moreover, increased pressure in the expansion portion 125 can enhance condensation of any vaporized gases.

When directly heating the sample 200 with radiation, it is generally desirable for the crucible portion 120 of the sample container 100 to be substantially or completely transparent to the radiation being used to heat the sample 200. For example, when using infrared radiation, it may be desirable for the sample container 100 to be made from quartz, which is substantially transparent to infrared radiation. This can help prevent hot spots on the crucible portion 120, and can also provide more even heating to the sample 200.

Referring again to FIG. 3, the second cooling mechanism 55 may include one or more fans. For example, there may be a first fan 60 for removing hot air from the heating compartment 30, and a second fan 62 for introducing cool air into the heating compartment 30. The first and second fans 60, 62 may be positioned on opposite sides of the heating compartment 30.

As shown, the second fan 62 may be configured to draw cool air into the heating compartment 30 from cooling compartment 35. In such cases, there may be a third fan 64 for directing air from the cooling compartment 35 towards the second fan 62.

Additionally or alternatively, the second fan 62 may be configured to draw in cool air from an external source such as room temperature air, or from another external source of cool air. In such cases, the container receptacle 20 may have one or more air intake apertures 66 extending through the housing 25 and into the heating compartment 30.

In some embodiments, one or more of the fans may be moveable such that they can be adjusted to remove air from the heating compartment 30 to the outside, or introduce air from the outside into the heating compartment 30. Other gas introduction systems are also possible instead of fans.

In some embodiments, one or more of the fans may have a variable speed. In such cases, the apparatus 10 may include a controller 68 for controlling speed of one or more of the fans. The controller 68 could also control the amount of time the fans are on or off during the digestion process In addition to controlling the fans, the controller 68 may also control other components of the apparatus 10 such as other cooling mechanisms including the Peltier cooler of the first cooling mechanism 50. Thus, the controller 68 can be used to control temperatures in both the heating compartment 30 and the cooling compartment 35.

The controller 68 may also operate the heating mechanism 40. More specifically, the output power of the infrared heater rings 42, 44 can be controlled and adjusted continuously and/or separately. This may allow the sample to reach a desired heating temperature for sample digestion. The heating time could also be controlled.

The controller 68 can also be configured to control cool-down times. For example, the controller 68 may activate the first or second cooling mechanisms after sample digestion is complete in order to cool down the sample container 100. This can allow users to pick up and handle the sample container 100 after digestion. In some cases, the cool-down time may be about 1-minute in comparison to 4-hours for previous hot block digestion devices.

Referring again to FIG. 1, the infrared heater rings 42, 44 are mounted within the heating compartment 30 and are positioned to encircle the crucible portion 120 of the sample container 100. In some cases, there may be a gap between the infrared heater rings 42, 44 and the crucible portion 120.

In some embodiments, one or more of the infrared heater rings 42, 44 may be moveable lengthwise along the sample container 100. This may allow the infrared heater rings 42, 44 to emit radiation along some of, or the entirety of the crucible portion 120. The infrared heater rings 42, 44 could be moved manually or through an actuator. As an example, the actuator could be controlled mechanically, electrically, or through computer software (e.g. using the controller 68).

The angular direction of the infrared heater rings 42, 44 could also be controlled, for example, to focus radiation at a narrow region or disperse radiation over a wider region. In some embodiments, the region may range from 10-mm to 45-mm in length along the crucible portion 120. The angular direction of the radiation may be adjusted using a gold coating on the infrared heater rings 42, 44, or using another reflective material such as quartz powder or a ceramic. The reflective material may be located on or near the infrared heater rings 42, 44.

The infrared heater rings 42, 44 may be configured to emit near-infrared wavelengths (e.g. 0.75-μm to 1.4-μm), short infrared wavelengths (e.g. 1.4-μm to 3-μm), medium infrared wavelengths (e.g. 3-μm to 8-μm), long infrared wavelengths (e.g. 8-μm to 15-μm), far-infrared wavelengths (e.g. 15-μm to 1000-μm), or combinations thereof. The controller 68 may select a specific infrared wavelength, for example, depending on the type of sample being digested or other aspects of the digestion being performed. For example, when the sample container 100 is made of quartz and the acid 210 is water-based, it may be desirable to select near-infrared wavelengths and short infrared wavelengths because quartz and water tend to have low absorption coefficients at these wavelengths. Thus, these wavelengths tend to allow more infrared radiation to be transmitted to the sample 200.

The controller 68 may also control the output energy of the infrared heater rings 42, 44. This may help maintain the sample 200 at a particular temperature for a particular time, for example, depending on the type of sample being digested or other aspects of the digestion being performed.

Referring now to FIG. 3, the container receptacle 20 will be described in greater detail. The housing 25 may be made from metals, plastics such as engineered plastics (e.g. acrylonitrile butadiene styrene or TEFLON™), or other suitable materials. The housing 25 generally defines the heating compartment 30 (also referred to as a "digester base"), and the cooling compartment 35. The heating compartment 30 and the cooling compartment 35 may be separated by an insulating region 70, which may include an insulating material such as insulation foam sandwiched between two plates 72. The insulating region 70 thermally insulates the cooling compartment 35 from the heating compartment 30. In some examples, the insulating region 70 may be omitted, and furthermore, in some embodiments, the heating and cooling compartments 30 and 35 may be combined in a single compartment.

The container receptacle 20 may include a support plate 74 for supporting the sample container 100. As shown, the support plate 74 may be located within the cooling compartment 35 and may have apertures (not shown) for allowing air flow throughout the cooling compartment 35.

The container receptacle 20 may include a removable cover 80. The cover 80 may define an upper compartment 82 located above the cooling compartment 35, which may accommodate an upper portion of the sample container 100 and possibly the lid 116. When the cover 80 is placed on the housing 25, the cover 80 may provide an air-tight seal around the sample container 100.

The cover 80 may also provide a second insulating region 84 between the cooling compartment 35 and the upper compartment 82. The second insulating region 84 may be similar to the first insulating region 70 and may include insulating material located between two plates 86. The second insulating region 84 thermally insulates the cooling compartment 35 from the upper compartment 82 and can help form a seal when the removable cover 80 is placed on top of the housing 25.

The container receptacle 20 may also include insulation around some or all of the housing 25. For example, as shown, there is insulation 96 around the cooling compartment 35. This may help keep the cooling compartment 35 at a desired temperature. In contrast, the housing 25 may have an open space 98 around the heating compartment 30, without insulation. This may promote air circulation between the open space 98 and the heating compartment 30.

The plates 72, 74, 86 within the container receptacle 20 generally have aligned apertures 90, 92, 94, respectively, for receiving the sample container 100. The aligned apertures 90, 92, 94 may define a cavity that is tubular or otherwise shaped to receive the sample container 100. The tubular cavity generally has an upper portion within the cooling compartment 35 for receiving the expansion portion 125 of the sample container 100, and a lower portion within the heating compartment 30 for receiving the crucible portion 120 of the sample container 100. When the sample container 100 is placed in the tubular cavity, a flared upper portion of the sample container 100 may be held on top of the top plate 86 between the second insulating region 84 and the condensing compartment 82. The remainder of the apertures 90, 92, 94 may be sized and shaped to provide air gaps or spaces between the plates 72, 74, 86 and the sample container 100.

With reference to FIGS. 1 and 3, the compartment 82 of the cover 80 may accommodate a condenser coil 130 and outlet 132 attached to the lid 116 of the sample container 100. The condenser coil 130 and outlet 132 may help condense and release volatile gases being produced during the digestion. In this sense, the compartment 82 may be referred to as a condenser chamber.

In some examples, the second insulating region 84 may have an aperture 134 for allowing cool air from the first cooling mechanism 50 to enter the condensing compartment 82. This may help condense the volatile gases.

The cover 80 may also include a pressure release chamber 150 separated from the condensing compartment 82 by a separator plate 152. The separator plate 152 may have an aperture 154 for receiving the outlet 132 of the condenser coil 130 such that the outlet 132 of the condenser coil 130 opens to the pressure release chamber 150. The aperture 154 may be sized and shaped to form a seal around the outlet 132 of the condenser coil 130.

The cover 80 may also have a pressure release aperture 156, which may release gases that accumulate with the pressure release chamber 150. These gases may be released to atmosphere or may be routed to a treatment device (e.g. through piping or a fume hood).

While the sample preparation apparatus 10 of the illustrated embodiment is configured to receive a single sample container 100, in other embodiments, the sample preparation apparatus may be configured to receive multiple sample containers.

Referring now FIG. 2, the sample container 100 will be described in greater detail. As described above, the tubular body 110 of the sample container 100 is generally sized and shaped to be received within the container receptacle 20 such that such that the expansion portion 125 is shaped to be received within the cooling compartment 35 and the crucible portion 120 is shaped to be received within the heating compartment 30, and specifically within the infrared heater rings 42, 44. In the illustrated embodiment, the elongate tubular body 110 of the sample container is generally cylindrical and tapers from the expansion portion 125 along the crucible portion 120 towards the bottom closed end 114. In this sense, the crucible portion 120 has a smaller diameter than the expansion portion 125. Furthermore, the crucible portion 120 has a smaller length than the expansion portion 125.

In other embodiments, the sample container 100 could have different shapes. For example, the sample container 100 might be a straight tube such that the crucible portion 120 and the expansion portion 125 have the same diameter.

As shown in FIG. 2, the crucible portion 120 may be double walled and may include an inner crucible wall 170 and an outer crucible wall 172 spaced apart from the inner crucible wall 170, which provides a space 174 therebetween. This space 174 can be a vacuum, or filled with a medium such as air, an inert gas, or a liquid. The medium may be selected to transmit the infrared radiation from the heating mechanism 40 to the sample 200 without appreciable loss of radiation energy.

The double walled crucible portion 120 can represent a safety measure. For example, the double walls may reduce or prevent the acid 210 from leaking into the heating compartment 30. In some cases, the medium within the space 174 may be selected to react with the acid 210 to act as a visual indicator of breakage to the inner crucible wall 170.

While the double walls can provide a safety measure, the double walls could also be used to enhance cooling of the acid 210. For example, the outer crucible wall 172 may have an inlet and an outlet (not shown) for supplying a coolant within the space 174 between the inner and outer crucible walls 170, 172. In such cases, the apparatus 10 may include a fluid circulating system (not shown) for circulating fluid between the crucible walls 170, 172, to thereby remove the heat from the crucible portion 120 and the acid 210.

In other embodiments, the sample container 100 may be single walled.

As described above, the sample container 100 may be made of a material that is substantially or completely transparent to the radiation being used to heat the sample 200. For example, when using infrared radiation, and particularly near-infrared or short infrared wavelengths, the sample container 100 may be made of quartz.

The sample container 100 may also be configured to withstand temperatures expected to be achieved within the crucible portion 120. For example, the sample container 100 may be made of high purity quartz or another suitable material that can withstand temperatures up to or above 1000° C.

The sample container 100 might also be made from a material that is resistant to decomposition by the acid 210 being used for sample digestion. For example, quartz tends to resist decomposition for a number of acids.

Furthermore, even if the sample container 100 might be susceptible to decomposition, cooling the crucible portion 120 can help reduce decomposition of the sample container. For example, when using hydrofluoric acid, a sample container made of quartz might otherwise decompose at hot digestion temperatures. Cooling the crucible portion 120 might help to reduce or prevent such decomposition of the quartz container.

While quartz has been described, the sample container 100 could also be made from other materials such as borosilicate glass (e.g. PYREX™ glass), or clear crystalline materials. In some cases, cooling the crucible portion 120 may allow the sample container 100 to be made from materials other than quartz, which is resistant to decomposition or breakdown at or below 1000 degrees Celsius. Less temperature resistant materials could be used.

As shown, the sample container 100 may include one or more graduation markings 180 such as a 25 mL mark, and a 50 mL mark. The markings 180 may assist a technician when adding the acid 210, or when adding a liquid to the sample container 100 so as to prepare a final volume of sample solution for subsequent chemical analysis.

In some embodiments, the sample container may also include a bar code. This may be useful during atomization of the digestion process.

Referring again to FIG. 1, the removable lid 116 may be made of PYREX™, TEFLON™, or another suitable material. The lid 116 is configured to enclose the sample container 100 and may be placed firmly on the open end 112, for example, using a pressure or twist fit. This may provide an airtight and/or leak proof seal. The middle of the lid 116 may have an aperture 117 (shown in FIG. 2), which may allow insertion of the condenser coil 130 into the sample container 100 to release pressure or unwanted gases from the sample container 100 such as carbon dioxide or nitrogen dioxide. The unwanted gases may be vented to the atmosphere, or may be subsequently treated or processed. The aperture 117 could also be used to allow oxygen or air to enter the sample container 100, for example, when ashing the sample 200.

In some embodiments, the lid 116 may have additional apertures. For example, a first aperture may receive an inlet tube (e.g. for receiving oxygen or air), and a second aperture may receive an outlet tube (e.g. for exhausting unwanted gases).

When using the sample container 100, the crucible portion 120 may serve as a digestion zone or a hot zone where the sample 200 is heated for digesting, dissolving or otherwise preparing samples for chemical analysis. Furthermore, the expansion portion 125 may serve as a refluxing area or cooled expansion zone where vaporized acid and other volatile vapors can initially expand, and then condense and reflux back to the crucible portion. This can prevent the loss of acid and other volatile components being analyzed. However, some of the unwanted reaction gases may be separated from the vaporized acid and other volatile vapors, for example, using the condenser coil 130, and those unwanted reaction gases can escape through the pressure release aperture 156 on the cover 80.

Figure 4:
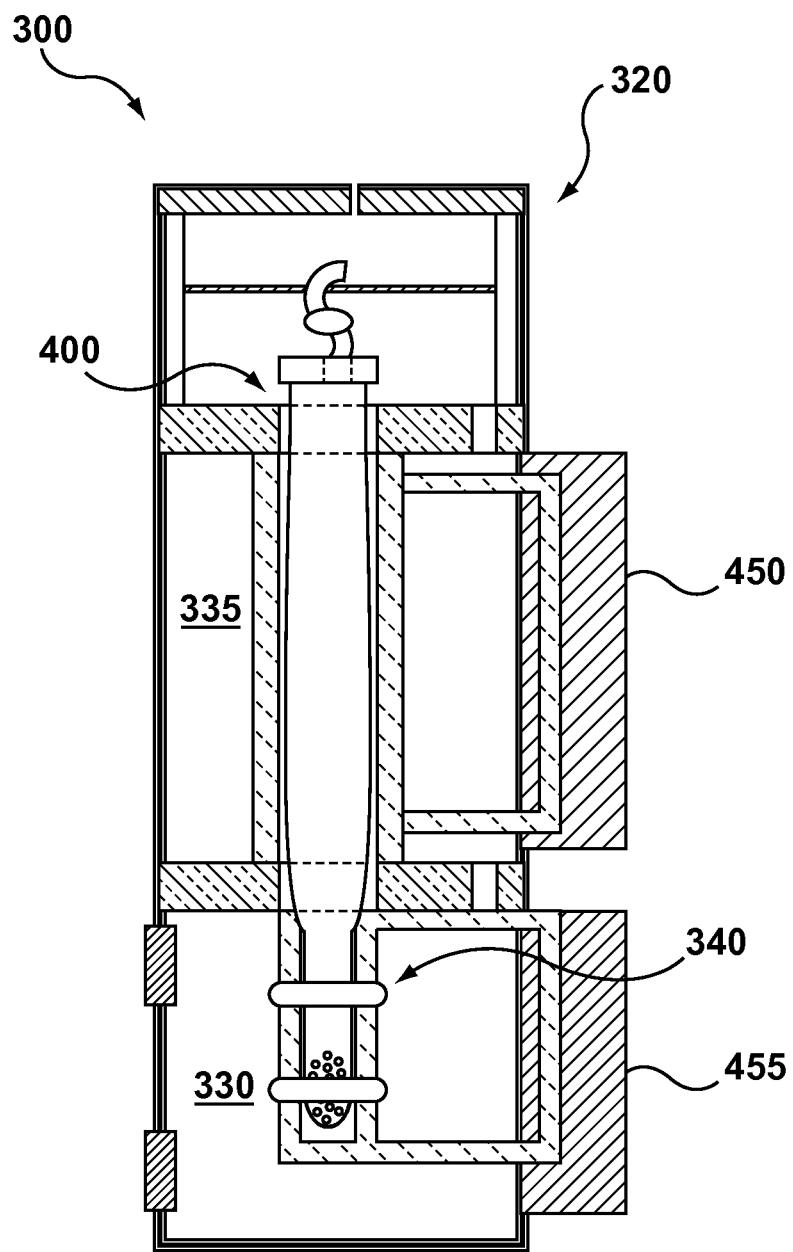
FIG. 4 is a schematic cross-sectional view of an apparatus for preparing samples for chemical analysis according to another embodiment.

Referring now to FIG. 4, illustrated therein in a sample preparation apparatus 300 made in accordance with another embodiment. The apparatus 300 is similar in some respects to the apparatus 10 and similar features are given similar reference numerals incremented by three hundred. For example, the apparatus 300 includes a container receptacle 320 for receiving a sample container 400, a heating mechanism 340, and one or more cooling mechanisms.

One difference is that the cooling mechanisms include refrigeration units 450, 455. More specifically, there is a first refrigeration unit 450 for circulating a coolant so as to cool the expansion portion 425 of the sample container 400, and a second refrigeration unit 455 for circulating a coolant so as to cool the crucible portion 420 of the sample container 400. The coolant may be a refrigerant such as anti-freeze, which may be capable of operating at temperatures below 0° C., and more particularly near −35° C. This can allow removal of greater amounts of heat than air circulation.

In some embodiments, a single refrigeration unit may circulate fluid around both the crucible portion 420 and the expansion portion 425.

As shown, refrigeration units 450, 455 may be closed heat exchanges having fluid conduits that wrap around the crucible portion 420 and the expansion portion 425 without having the coolant directly contact the sample container 400. In other embodiments, the refrigeration units 450, 455 may be open heat exchanges having the coolant directly in contact with the sample container 400.

Figure 5:
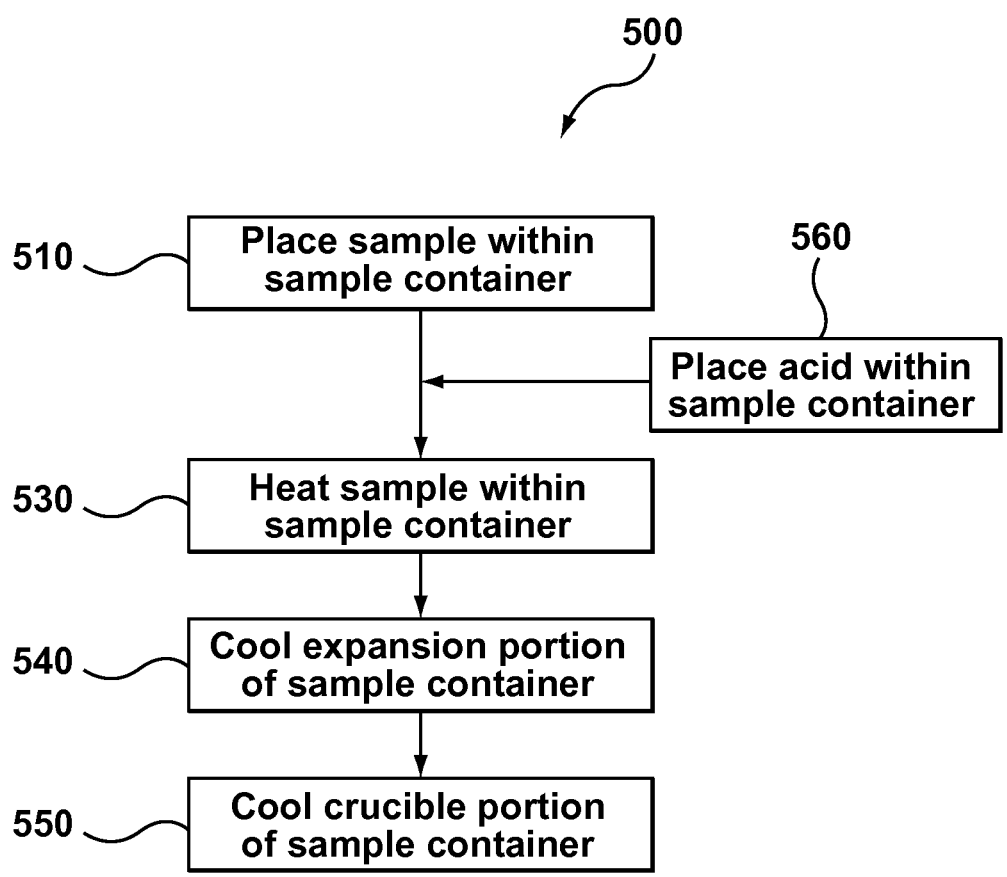
FIG. 5 is a flow chart showing a method for preparing samples for chemical analysis according to another embodiment.

Referring now to FIG. 5, illustrated therein is a method 500 for preparing samples for chemical analysis. The method 500 generally includes steps 510-550, described as follows.

Step 510 includes placing a sample within a sample container such as one of the sample containers 100, 400. The sample container generally has a crucible portion and an expansion portion. The crucible portion generally contains the sample and a liquid reactant such as an acid.

Step 530 includes heating the sample within the crucible portion of the sample container while the sample container is received within the container receptacle. For example, the sample may be heated using a heating mechanism such as the infrared heater rings 42, 44 or another source of infrared radiation. In some embodiments, the infrared heater rings may be positioned or oriented to emit radiation toward a particular region of the crucible portion, for example, in accordance to the type and size of sample, or other aspects of the digestion being performed.

In some embodiments, the infrared radiation may be selected to be absorbed by the sample in the crucible portion of the sample container. Moreover, the crucible portion may be substantially or completely transparent to the selected infrared radiation. For example, the sample container may be made of quartz.

In some embodiments, step 530 of heating the sample may occur after placing the sample container into a container receptacle such as the container receptacles 20, 320.

Step 540 includes cooling the expansion portion of the sample container while the sample container is received within the container receptacle. For example, the expansion portion may be cooled using a cooling mechanism such as a Peltier cooler, one or more fans, or a refrigeration unit.

Step 550 includes cooling the crucible portion of the sample container while the sample container is received within the container receptacle. For example, the crucible portion may be cooled using a cooling mechanism such as one or more fans or a refrigeration unit.

Steps 540 and 550 generally occur contemporaneously with step 530 of heating the sample. More specifically, while steps 540 and 550 occur within the same general time period as step 530, the steps may occur before, after, or concurrent with each other.

The method 500 may also include step 560, which includes placing the acid within the crucible portion of the sample container. The acid may be used to digest or otherwise dissolve the sample while heating the sample. In some embodiments, the acid may include hydrofluoric acid, which may be used to digest or otherwise dissolve silicates.

The method 500 may include providing oxygen to the crucible portion of the sample container so as to burn the sample into ash while heating the sample.

The method 500 may include providing a flux to the crucible portion of the sample container for fusion extraction prior to providing the acid.

The method 500 may include adjusting one or more of speed, position, or orientation corresponding to one or more fans used for cooling the expansion portion or crucible portion. Adjustments to the fans may be based upon the type and size of sample, or other aspects of the digestion being performed.

Testing was completed using an apparatus similar to the apparatus 10 described above. One difference is that three infrared heater rings were used. Specifically, the infrared heater rings were sold by Anderson Thermal Devices Inc. under product number OMG02511549C45. Furthermore, a tube body refrigeration unit was used to cool the expansion portion of the sample container using a coolant. A water cooled condenser coil was fitted onto the lid of the sample container. The sample container was made from quartz and had an overall length of 174-mm. The crucible portion had a length of 50-mm length and a diameter of 16.65-mm. The expansion portion had a length of 103-mm and a diameter of 27.2-mm. The tapered portion between the expansion portion and crucible portion had a length of 21-mm.

Figure 6:
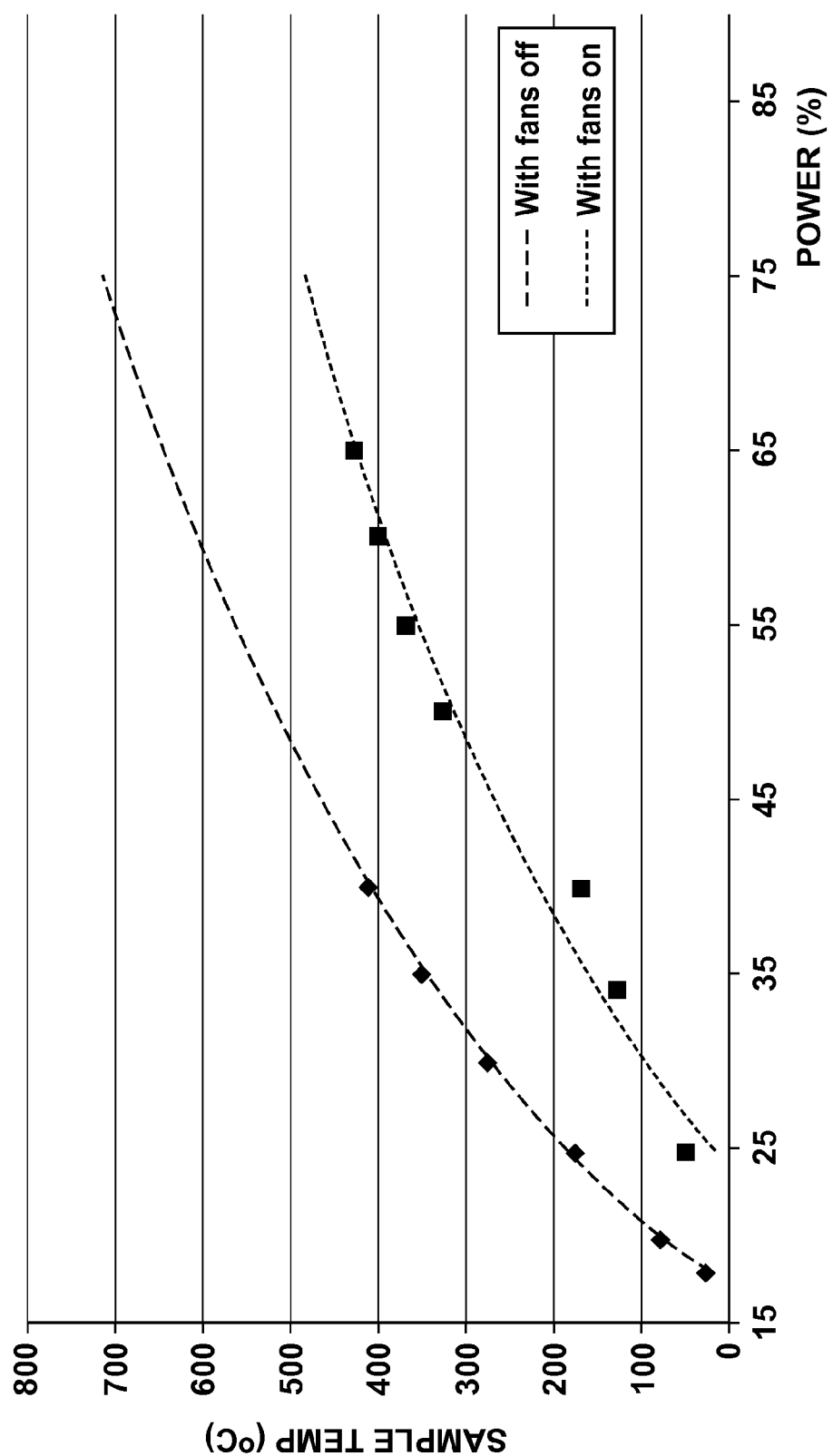
FIG. 6 is a graph showing temperature versus power for a test completed using an apparatus operating in two modes, namely, the fan turned on, and the fan turned off.

A test was performed with the fans in the heating compartment operated on and off during digestion. In this test, a thermocouple probed temperature within the crucible portion of the sample container. Clean white sand was loaded into the crucible portion to simulate a digestion sample. FIG. 6 shows the temperature profiles vs. power for the fan on and off. The temperature difference between the fan-on and fan-off modes indicates that heat removal from the heating compartment can be effective at lowering temperature within the digestion zone. As described above, this can help reduce or prevent boiling of the acid.

Another test was completed to compare sample digestion with one fan cooling the crucible portion, and two fans cooling the crucible portion. The test samples included an SCP contaminated soil sample (SCP SS-1) and a NIST 8600 copper ore sample (NIST 8600). The samples were prepared using reagent-grade (single distilled) nitric acid (68-70% m/v) and hydrochloric acid (36.5 38% m/v). Sample and working solutions were prepared with ultra-pure de-ionized water (18.2 MS2 resistivity).

Approximately 0.2-0.5 grams of dried samples were added to the sample container. As a preliminary step, 2 mL of concentrated $HNO_3$ was added to the sample and then irradiated. This preliminary step was aimed at removing organic carbon content and helping to prevent foaming in a subsequent aqua regia leaching stage. After reddish fumes corresponding to $NO_2$ dissipated (indicating the end of the oxidation reaction), the sample container was left to cool for one minute. Afterwards, 3 mL of concentrated HCl was added to form a modified aqua regia leaching mixture. The sample was irradiated in order to digest the sample. During the digestion, input energy was controlled to limit boiling of the acid. After digesting the sample, 2 mL of $H_2O_2$ was added to further oxidize carbon residues and convert remaining $NO_x$ to $NO_3^-$. The sample was then irradiated again to enhance this oxidization.

After digestion, the samples were analyzed using a PerkinElmer OPTIMA® DV3300 ICP-OES mass spectrometer and compared to analytical information obtain from corresponding samples digested using a hot block. The percentage recovery of six metals (Cr, Cu, Fe, Mn, Ni, and Zn) for the SCP SS-1 sample is shown in Table 1, and the percentage recovery of five metals (Cu, Fe, Zn, Mn, and Ca) for the NIST 8600 sample is shown in Table 2. Overall digestion times are also shown in each table.

TABLE 1

Percentage Recovery and Digestion Times for SCP SS-1

|  | Cr (%) | Cu (%) | Fe (%) | Mn (%) | Ni (%) | Zn (%) | Digestion Time (min) |
|---|---|---|---|---|---|---|---|
| One Fan | 86.5 | 105.6 | 107.1 | 110.4 | 104.5 | 111.1 | 25 |
| Two Fans | 111.4 | 111.4 | 110.4 | 112.0 | 107.3 | 116.6 | 12 |
| Hot Block | 88.0 | 122.0 | 62.0 | 95.0 | 90.0 | 89.0 | 240 |

TABLE 2

Percentage Recovery and Digestion Times for NIST 8600

|  | Cu (%) | Fe (%) | Zn (%) | Mn (%) | Ca (%) | Digestion Time (min) |
|---|---|---|---|---|---|---|
| One Fan | 105.1 | 93.7 | 101.3 | 102.8 | 99.7 | 30 |
| Two Fans | 104.1 | 106.2 | 99.5 | 104.4 | 100.7 | 13 |

The results show that the percentage recovery of the metals was between 86.5% and 116.6% when using either one or two fans. These results are better than the percentage recovery for the hot block, which was between 62.0% and 122.0%.

Furthermore, digestion times were significantly faster when using one or two fans in comparison to the hot block method. It is understood that the faster digestion times were possible because input energy could be increased when using the fans. Specifically, with one fan on, the maximum power applied to the infrared heaters was 140 W. Above that power threshold, the acid began boiling vigorously. With two fans on, the maximum power applied to the infrared heaters could be increased to 210 W without vigorous boiling. Accordingly, the use of two fans indicates that cooling the crucible more can allow increased input energy.

The results support the above-noted theory, although it is contrary to the standard theory that "more heat energy would provide better and faster sample digestion." Contrary to this standard theory, one or more of the embodiments herein may be described as operating on an inverse theory of "less excess heat energy may provide better and faster the digestion". In this latter case, sample digestion can be influenced by radiation absorbed by the sample and excess heat energy is removed to inhibit or prevent liquid vaporization, which in turn, can allow more input radiation energy. Overall, this can enhance quality and speed of sample digestion.

In view of the above, one or more embodiments herein may be capable of enhancing chemical dynamics of the digestion process, which can help achieve faster or more complete digestion. Volatile analyte and reactants can also be preserved, which can lead to better recovery of analyte elements of interest.

It will be understood that the apparatus, systems and methods herein may be computer automated or robotically automated, for example, by mechanical, electrical, or computer software devices.

It will also be understood that the apparatus, systems and methods herein may be capable of providing single step sample preparation, including drying, ashing, and/or wet acid-digestion of samples, for subsequent chemical analysis of various parameters.

While the above description provides examples of one or more apparatus, methods, or systems, it will be appreciated that other apparatus, methods, or systems may be within the scope of the present description as interpreted by one of skill in the art.

The invention claimed is:

1. An apparatus for preparing samples for chemical analysis, the apparatus comprising:
   (a) a container receptacle for receiving at least one sample container having a crucible portion and an expansion portion, the container receptacle comprising a heating compartment and a cooling compartment spaced apart from the heating compartment, the heating compartment being shaped to receive the crucible portion of the sample container, and the cooling compartment being shaped to receive the expansion portion of the sample container;
   (b) a heater for directly heating the sample within the crucible portion of the sample container while the sample container is received within the container receptacle;
   (c) a first cooler for cooling the expansion portion of the sample container while the expansion portion is received within the cooling compartment; and
   (d) a second cooler for providing cooling air to the crucible portion of the sample container to cool the crucible portion contemporaneously with the direct heating of the sample while the crucible portion is received within the heating compartment without reducing the direct heating applied to the sample by the heater.

2. The apparatus of claim 1, wherein the second cooler comprises a fan located within the heating compartment.

3. The apparatus of claim 2, wherein the fan has a variable speed.

4. The apparatus of claim 3, further comprising a controller for controlling speed of the fan.

5. The apparatus of claim 1, wherein the first cooler comprises a thermoelectric cooler within the cooling compartment.

6. The apparatus of claim 1, wherein the first cooler comprises a refrigeration unit within the cooling compartment.

7. The apparatus of claim 1, wherein the second cooler comprises a refrigeration unit within the heating compartment.

8. The apparatus of claim 1, wherein the first cooler is integral with the second cooler to cool both the expansion portion and the crucible portion of the sample container.

9. The apparatus of claim 1, wherein the heater includes an infrared heater disposed within the heating compartment for emitting infrared radiation.

10. A system for preparing samples for chemical analysis, the system comprising:
    (a) a sample container including an elongate tubular body extending from an open end to a closed end, a crucible portion proximal to the closed end for holding a sample to be analyzed, and an expansion portion proximal to the open end;
    (b) a container receptacle for receiving the sample container, the container receptacle comprising a heating compartment, and a cooling compartment spaced apart from the heating compartment, the heating compartment being shaped to receive the crucible portion of the sample container, and the cooling compartment being shaped to receive the expansion portion of the sample container;
    (c) at least one heater for directly heating the sample within the crucible portion of the sample container while the sample container is received within the container receptacle;
    (d) a first cooler for cooling the expansion portion of the sample container while the expansion portion is received within the cooling compartment; and
    (e) a second cooler for providing cooling air to the crucible portion of the sample container to cool the crucible portion contemporaneously with the direct heating of the sample while the crucible portion is received within the heating compartment without reducing the direct heating applied to the sample by the at least one heater.

11. The system of claim 10, wherein the heater is configured to emit infrared radiation that is selected to be absorbed by the sample in the crucible portion of the sample container, and wherein the crucible portion is transparent to the infrared radiation.

12. The system of claim 11, wherein the sample container is made of quartz.

13. The system of claim 11, wherein the heater includes an infrared heater disposed within the heating compartment for emitting the infrared radiation.

14. The system of claim 13, wherein the infrared heater includes at least two infrared heater rings that are sized and shaped to receive and encircle the crucible portion of the sample container.

15. The system of claim 14, wherein at least one of the infrared heater rings is moveable lengthwise along the crucible portion of the sample container.

16. A method for preparing samples for chemical analysis, the method comprising:
    (a) placing a sample within a sample container containing an acid into a container receptacle, the container receptacle comprising a heating compartment and a cooling compartment spaced apart from the heating compartment, the sample container having a crucible portion for receiving the sample and an expansion portion, the heating compartment being shaped to receive the crucible portion of the sample container, and the cooling compartment being shaped to receive the expansion portion of the sample container;
    (b) directly heating the sample with a heater within the crucible portion of the sample container, while the sample container is received within the container receptacle;
    (c) cooling, with a first cooler, the expansion portion of the sample container contemporaneously with the heating of the sample, while the expansion portion is received within the cooling compartment; and
    (d) providing cooling air, with a second cooler, to the crucible portion of the sample container to cool the crucible portion contemporaneously with the direct heating of the sample, while the crucible portion is received within the heating compartment, without reducing the direct heating applied to the sample by the heater.

17. The method of claim 16, wherein the second cooler cools the crucible portion using at least one fan.

18. The method of claim 16, wherein the first cooler cools the expansion portion using a thermoelectric cooler.

19. The method of claim 16, wherein at least one of the first or second cooler cools the expansion portion and the crucible portion using at least one refrigeration unit.

20. The method of claim 16, wherein the heater heats the sample using infrared radiation that is selected to be absorbed by the sample in the crucible portion of the sample container, and wherein the crucible portion is transparent to the infrared radiation.

21. The method of claim 20, wherein the sample container is made of quartz.

22. The method of claim 16, further comprising placing the acid within the crucible portion of the sample container.

23. The method of claim 22, wherein the acid includes hydrofluoric acid.

24. The method of claim 16, wherein the heater heats the sample using at least one infrared heater ring that is sized and shaped to receive and encircle the crucible portion of the sample container, and wherein the method further comprises moving the infrared heater ring lengthwise along the crucible portion of the sample container.

25. The method of claim 24, wherein the heater heats the sample using at least two infrared heater rings.

26. The method of claim 16, further comprising placing the sample container into a container receptacle prior to heating the sample.

27. An apparatus for preparing samples for chemical analysis, the apparatus comprising:

(a) a container receptacle for receiving at least one sample container having a crucible portion and an expansion portion, the container receptacle comprising a heating compartment and a cooling compartment spaced apart from the heating compartment, the heating compartment being shaped to receive the crucible portion of the sample container, and the cooling compartment being shaped to receive the expansion portion of the sample container;

(b) a heater for directly heating the sample within the crucible portion of the sample container while the sample container is received within the container receptacle;

(c) at least one cooler for providing cooling air to the expansion portion and the crucible portion of the sample container to cool the expansion portion and to cool the crucible portion contemporaneously with the direct heating of the sample while the expansion portion is received within the cooling compartment and while the crucible portion is received within the heating compartment and without reducing the direct heating applied to the sample by heater.

28. The apparatus of claim 27, wherein the at least one cooler includes a first cooler for cooling the expansion portion of the sample container, and a second cooler for cooling the crucible portion of the sample container.

* * * * *